United States Patent [19]

Slongo et al.

[11] Patent Number: 4,892,915
[45] Date of Patent: Jan. 9, 1990

[54] COPOLYMERS OF 2-(2-HYDROXY-5-ACRYLOYLOXYALKYL)-PHENYL-2H-BENZOTRIAZOLES

[75] Inventors: Mario Slongo, Tafers; Jean Rody, Riehen, both of Switzerland

[73] Assignee: Ciba-Geigy Corporation, Ardsley, N.Y.

[21] Appl. No.: 218,188

[22] Filed: Jul. 13, 1988

Related U.S. Application Data

[62] Division of Ser. No. 886,934, Jul. 18, 1986, Pat. No. 4,785,063.

[30] Foreign Application Priority Data

Jul. 26, 1983 [CH] Switzerland .......................... 4087/83

[51] Int. Cl.$^4$ ........................................... C07D 249/16
[52] U.S. Cl. .................................................... 526/259
[58] Field of Search ........................................ 526/259

[56] References Cited

U.S. PATENT DOCUMENTS 4,612,358  9/1986  Besecke et al. ...................... 526/259
4,652,656  3/1987  Besecke et al. ...................... 526/259
4,785,063  11/1988  Slongo et al. ....................... 526/259

Primary Examiner—John Kight
Assistant Examiner—Kriellion Morgan
Attorney, Agent, or Firm—Luther A. R. Hall

[57] ABSTRACT

Compounds of the formula I

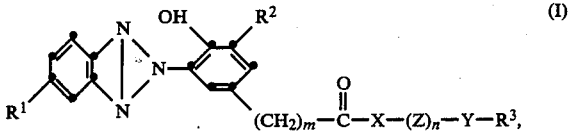

is hydrogen, chlorine, lower alkyl or lower alkoxy, $R^2$ is hydrogen or alkyl, $R^3$ is lower alkenoyl, X and Y are independently —O— or —NH—, m is 0, 1 or 2 and n is 0 or 1, are suitable as copolymerisable UV stabilizers for polymers obtainable from ethylenically unsaturated monomers. The compounds of the formula I are readily obtainable, and are particularly valuable as UV absorbers by virtue of their good solubility in copolymerisable monomers.

1 Claim, No Drawings

COPOLYMERS OF 2-(2-HYDROXY-5-ACRYLOYLOXYALKYL)PHE-NYL-2H-BENZOTRIAZOLES

This is a divisional of application Ser. No. 886,934, filed on July 18, 1986, now U.S. Pat. No. 4,785,063, issued on Nov. 15, 1988, which in turn is a continuation of application Ser. No. 802,071, filed on Nov. 26, 1985, now abandoned, which in turn is a continuation of application Ser. No. 631,276, filed on July 16, 1984, now abandoned.

The present invention relates to novel copolymerisable 2-(2'-hydroxyphenyl)-benzotriazoles, to their use for the protection of polymers against light-induced degradation, and to the polymers to which the protective finish has been imparted.

The method of adding ethylenically unsaturated derivatives of benzotriazoles to polymerisable monomers and then reacting these to obtain copolymers protected against UV light is known. Incorporable stabilisers of this type are described for example in the U.S. Pat. No. 3,399,173. Known copolymerisable additives are however insufficiently soluble in the co-monomer, and this leads to a breakdown of copolymerisation; or in some cases they are difficult to obtain. Furthermore, there are described in the European Patent Application No. 57160 benzotriazole UV absorbers which can be used for, inter alia, lacquer systems, such as automobile lacquers. The compounds according to the invention do not have the disadvantages mentioned, or have them to a lesser extent, and they have in addition the advantage of having high stability to migration and of providing the possibility of using high concentrations of UV absorber in thin layers, for example protective layers. It is of importance in this respect that the other properties of the polymer to be protected are changed either not at all or only insignificantly.

The present invention relates to compounds of the formula I

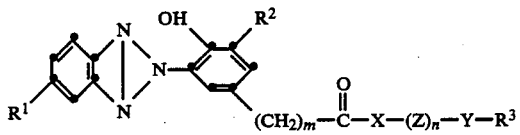

wherein
X is —O— or —N($R^4$)—,
Y is —O— or —N($R^5$)—,
Z is $C_2$–$C_{12}$-alkylene, $C_4$–$C_{12}$-alkylene interrupted by one to three nitrogen and/or oxygen atoms, or is $C_3$–$C_{12}$-alkylene, butenylene, butynylene, cyclohexylene or phenylene, each substituted by a hydroxyl group,
m is zero, 1 or 2,
n is 1 and, when X and Y are —N($R^4$)— and —N($R^5$)—, respectively, is also zero,
$R^1$ is hydrogen, chlorine, $C_1$–$C_4$-alkyl or $C_1$–$C_4$-alkoxy,
$R^2$ is hydrogen or $C_1$–$C_8$-alkyl, and
$R^3$ is a group —C(O)—C($R^6$)=C(H)$R^7$ or, when Y is —N($R^5$)—, forms together with $R^5$ a group —C(O)—CH=CH—C(O)—, wherein $R^6$ is hydrogen or methyl, and $R^7$ is hydrogen, methyl or —C(O)—X—$R^8$, wherein $R^8$ is hydrogen, $C_1$–$C_{12}$-alkyl or a group of the formula

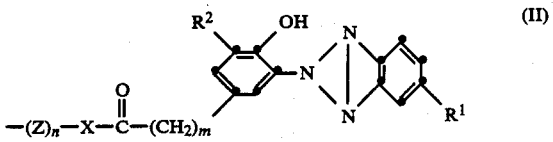

wherein the symbols $R^1$, $R^2$, X, Z, m and n have the meanings defined above, and $R^4$ and $R^5$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{11}$-aralkyl, and $R^4$ together with $R^5$, in the case where Z is ethylene, also forms ethylene.

X and Y independently of one another can be —O— or —N($R^4$)— and —N($R^5$)—, respectively. To be emphasised are compounds in which one of X and Y is —O—; and particularly those in which both X and Y are —O—.

As $C_2$–$C_{12}$-alkylene, Z is straight-chain or branched-chain. It is for example: ethylene, propylene, tetramethylene, hexamethylene, octamethylene, dodecamethylene, 1,1-ethylidene, 2,2-propylidene, 2-methylpentamethylene or 2-ethylhexamethylene. $C_2$–$C_6$-alkylene groups are preferred.

When Z is $C_4$–$C_{12}$-alkylene which is interrupted by oxygen, it is for example: —$CH_2$—$CH_2$—O—$CH_2$—$CH_2$—, —$CH_2$—$CH_2$—O—$CH_2$—$CH_2$—$CH_2$, $CH_2$—$CH_2$—O—$CH_2$—$CH_2$—O—$CH_2$—$CH_2$ or —$CH_2$—$CH_2$—O—$CH_2$—$CH_2$—O—$CH_2$—$CH_2$—O—$CH_2$—$CH_2$—, and, if alkylene is interrupted by nitrogen, a group —N($R^4$)— is meant, wherein $R^4$ is as defined in the foregoing, for example —$CH_2$—$CH_2$—NH—$CH_2$—$CH_2$—$CH_2$—$CH_2$, —$CH_2$—$CH_2$—$CH_2$—NH($CH_2$)$_8$— or —$CH_2$—$CH_2$—$CH_2$—N($CH_3$)—$CH_2$—CH($C_2H_5$)($CH_2$)$_4$—.

As $C_3$–$C_{12}$-alkylene substituted by a hydroxyl group, Z is 2-hydroxytetramethylene, 2-hydroxyhexamethylene and, in particular, 2-hydroxypropylene.

As cyclohexylene, Z is for example cyclohexylene-1,4 and, in particular, cyclohexylene-1,2.

As phenylene, Z is for example phenylene-1,3 or phenylene-1,4.

m can be zero, 1 or 2, but it is preferably 2.

n is preferably 1, but can also be zero if both X and Y are bound by way of nitrogen.

As $C_1$–$C_4$-alkyl, $R^1$ is for example: methyl, ethyl, n-propyl, isopropyl, n-butyl, sec-butyl or tert-butyl.

When $R^1$ is $C_1$–$C_4$-alkoxy, it is for example: methoxy, ethoxy, n-propoxy, isopropoxy, n-butoxy or tert-butoxy.

A preferred meaning of $R^1$ is hydrogen or chlorine.

As $C_1$–$C_8$-alkyl, $R^2$ is for example: methyl, ethyl, n-propyl, isopropyl, n-butyl, sec-butyl, tert-butyl, n-pentyl, tert-amyl, n-hexyl, n-heptyl, n-octyl, 2-ethylhexyl or 1,1,3,3-tetramethylbutyl. Tert-butyl is preferred.

As $C_1$–$C_{12}$-alkyl, $R^4$, $R^5$ and $R^8$ can have the same meaning as that given in the foregoing for $R^2$, and can additionally be straight-chain or branched-chain nonyl, decyl, undecyl or dodecyl.

When $R^4$ and $R^5$ are alkyl interrupted by oxygen atoms, the examples which apply are the same as those described in the foregoing for Z.

Examples for $R^4$ and $R^5$ as aralkyl are: benzyl, α-methylbenzyl, 1-phenylethyl, α,α-dimethylbenzyl or 1-phenylpropyl.

If Z is ethylene, $R^4$ and $R^5$ together can likewise form ethylene, which is equivalent to a bridging over by way of a piperazine group.

When Y is a group $-N(R^5)-$, $R^3$ and $R^5$ together make up a group $-C(O)-CH=CH-C(O)-$, and thus form the substituent

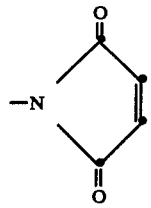

on the group $-X-(Z)_n-$.

The preferred meaning of $R^3$ is however $-C(O)-C(R^6)=C(H)R^7$.

$R^6$ and $R^7$ are preferably methyl and especially hydrogen.

Particularly preferred are compounds of the formula I wherein X is $-O-$ or $-N(R^4)-$ and Y is $-O-$ or $-N(R^5)-$, Z is $C_2-C_6$-alkylene, 2-hydroxypropylene or cyclohexylene, m is 2 and n is 1, $R^1$ is hydrogen or chlorine, $R^2$ is hydrogen or $C_1-C_8$-alkyl, and $R^3$ is a group $-C(O)-C(R^6)=C(H)R^7$, wherein $R^6$ and $R^7$ independently of one another are hydrogen or methyl, and $R^3$, when Y is $-N(R^5)-$, forms together with $R^5$ a group $-C(O)-CH=CH-C(O)-$, and $R^4$ and $R^5$ independently of one another are each hydrogen or $C_1-C_4$-alkyl.

Examples of compounds of the formula I are those corresponding to the formula II (II)

| A | B | C |
|---|---|---|
| H or Cl | $-tert.C_4H_9$ | $-CH_2CH_2C(O)NH-CH_2CH_2OC(O)CH=CH_2$ |
| H or Cl | $-tert.C_4H_9$ | $-CH_2CH_2C(O)O-$⟨cyclohexyl-H⟩$-OC(O)-CH=CH_2$ |
| H or Cl | $-tert.C_5H_{11}$ | $-CH_2CH_2C(O)NHCH_2CH_2-N$⟨maleimide⟩ |
| H or Cl | $-C(CH_3)_2CH_2C(CH_3)_3$ | $-CH_2CH_2C(O)NHNHC(O)CH=CH_2$ |
| H or Cl | $-sec.C_4H_9$ | $-CH_2CH_2C(O)OCH_2CH_2NHC(O)C(CH_3)=CH_2$ |
| $-CH_3$ | $-tert.Butyl$ | $-CH_2CH_2C(O)OCH_2CH_2OC(O)C(CH_3)=CH_2$ |
| $-OCH_3$ | $-tert.C_5H_{11}$ | $-C(O)NH-(CH_2)_6NHC(O)CH=CH_2$ |
| H or Cl | $-tert.C_4H_9$ | $-CH_2CH_2C(O)O-CH_2CH_2OCH_2CH_2-OC(O)CH=CH_2$ |
| H or Cl | $-tert.C_5H_{11}$ | $-CH_2CH_2C(O)O-CH_2CH_2CH_2CH_2OC(O)CH=C(H)CH_3$ |
| H or Cl | $-tert.C_4H_9$ | $-CH_2CH_2C(O)N(CH_3)CH_2CH_2N(CH_3)C(O)CH=CH_2$ |
| $CH_3$ | $-iso-C_3H_7$ | $-CH_2CH_2C(O)OCH_2CH_2N(C_4H_9)C(O)C(CH_3)=CH_2$ |
| H or Cl | $-tert.C_4H_9$ | $-CH_2CH_2C(O)O-$⟨phenylene⟩$-OC(O)CH=CH_2$ |
| H or Cl | $-tert.C_4H_9$ | $-CH_2CH_2C(O)N$⟨piperazine⟩$NC(O)CH=CH_2$ |
| $-OCH_3$ | $-tert.C_4H_9$ | $-CH_2C(O)NHCH_2CH_2OC(O)C(CH_3)=C(H)CH_3$ |

-continued

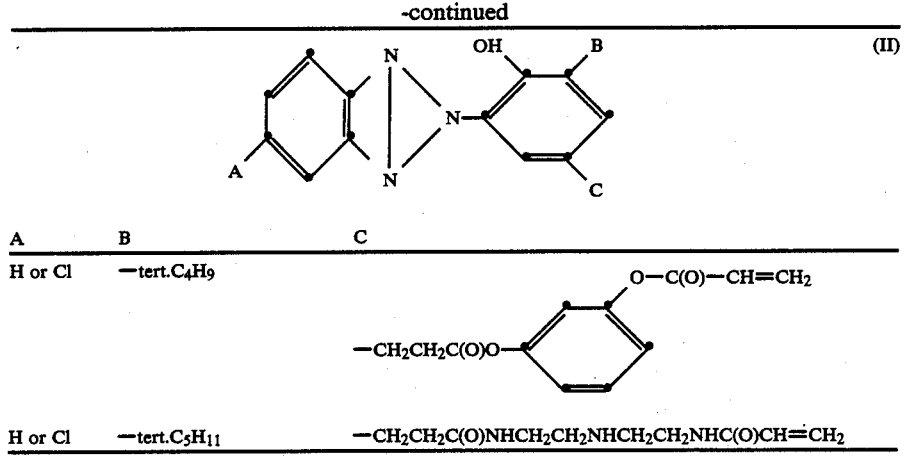

| A | B | C |
|---|---|---|
| H or Cl | —tert.C₄H₉ | —CH₂CH₂C(O)O—⌬—O—C(O)—CH=CH₂ |
| H or Cl | —tert.C₅H₁₁ | —CH₂CH₂C(O)NHCH₂CH₂NHCH₂CH₂NHC(O)CH=CH₂ |

The compounds of the formula I are produced in a manner known per se. Thus, for example, an unsubstituted or substituted o-nitroaniline is diazotised, and the diazotised product is coupled, at a pH value of about 8 to 11, with a compound of the formula III

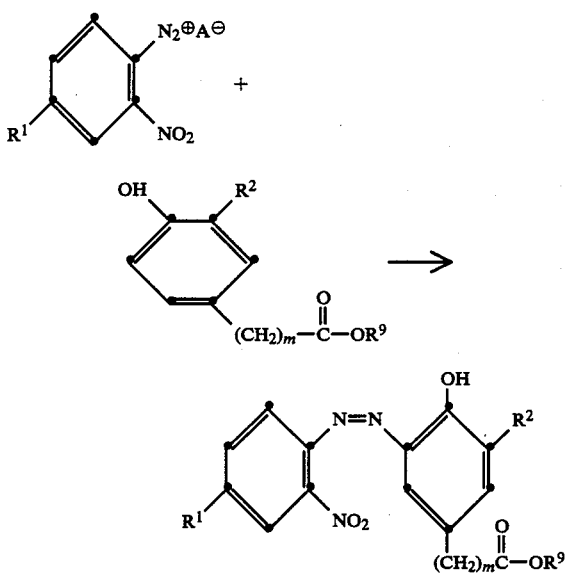

The symbols $R^2$ and m are as defined in the foregoing, and $R^9$ is hydrogen or lower alkyl. The reaction proceeds according to the following reaction pattern:

The symbol X denotes an anion such as Cl⁻, —HSO₄⁻ or (BF₄)⁻. There is produced from the product, obtained for example as described above, by a reducing cyclisation under alkaline conditions, the corresponding benzotriazole derivative:

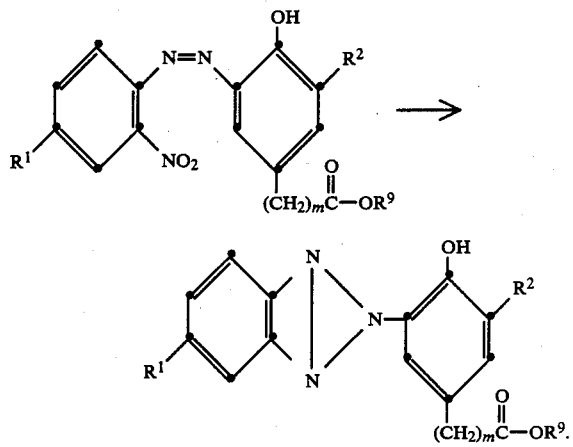

In the case of a reductive cyclisation, the reaction is preferably performed catalytically by means of hydrogen, or there is used for example zinc dust as the reducing agent. As a result of the alkaline medium, the ester ($R^9$) indeed becomes saponified; it can however, after acidification, be easily produced again by boiling in a lower alkyl alcohol, such as methanol.

The product thus obtained in an intermediate to be reacted for example with compounds of the formula HX—(Z)ₙ—YH. This involves a customary transesterification leading to compounds of the formula

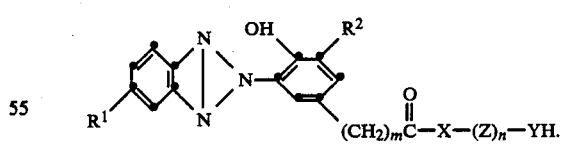

These can be esterified in a known manner with chloropropionic acid chloride to give the compounds of the formula I. The various process steps are known to a person skilled in the art, and are described in detail in the European Patent Application No. 57 160.

The 2-(2'-hydroxyphenyl)-benzotriazole compounds usable according to the invention can constitute between 0.01 and 20% of the polymerisable mixtures. When the formed copolymer is processed directly into articles having a thickness exceeding 0.1 mm, contents of 0.05 to 2%, relative to the total weight, are preferred;

with polymers which are used as very thin coatings, and also with polymers which are to be incorporated as stock concentrates of conventionally produced polymers, contents of 2–20% are preferred. In this case, the colourless benzotriazole compounds are particularly valuable, since, with such high concentrations, there can readily occur severe yellowing.

The following may be mentioned as examples of ethylenically unsaturated compounds suitable for producing the copolymers according to the invention:

1. monosubstituted ethylenes, that is, vinyl compounds, such as vinyl halides, for example vinyl fluoride or vinyl chloride; vinyl esters of organic carboxylic acids, for example vinyl acetate, vinyl stearate or vinyl benzoate; vinyl ethers, for example vinylisopropyl ether of vinylphenyl ether; vinyl ketones, for example vinylmethyl ketone or vinylcyclohexyl ketone; N-vinyl compounds, for example vinyl pyrrolidone, vinyl carbazol or vinylisocyanate; S-vinyl compounds, such as vinylmethyl thioether, vinylmethylsulfone or vinylsulfonic acid; vinyl-substituted homocyclic- or heterocyclic-aromatic compounds, such as styrene, vinyltoluene, 1-vinylnaphthalene or 2-vinylpyridine; acrylic compounds, for example acrylic acid, acrylonitrile, phenyl acrylate, ethyl acrylate, acrylic acid amide or acrylic acid butylamide; allyl compounds, such as esters and ethers of allyl alcohol, for example allylbenzoate or phenylallyl ether; derivatives of allylamine, such as acetic acid allylamide, allylurea or N-allyl-2,4,6-triamino-1,3,5-triazine, or C-allyl compounds, such as allylbenzene;

2. 1,1-disubstituted ethylenes, that is, vinylidene compounds, for example vinylidene chloride, vinylidene cyanide, methacrylonitrile, methyl methacrylate, α-chloroacrylic acid ethyl ester, α-methylstyrene, isobutylene or isopropenyl acetate;

3. 1,2-disubstituted ethylenes, such as vinylenecarbonate, maleic acid anhydride, maleic acid imide, fumaric acid ethyl ether, maleic acid dinitrile, acenaphthalene or S,S-dioxobenzothiophene; and 4. di- and polyenes, particularly conjugated polyenes, such as butadiene, isoprene, chloroprene, sorbic acid or sorbic acid methyl ester, or compounds having several isolated double bonds, such as divinyl benzene, acrylic acid allyl ester, phthalic acid diallyl ester, glucosetriallyl ether or N,N',N''-triallyl-2,4,6-triamino-1,3,5-triazine.

The homopolymerisable monomers of the stated monomers can be copolymerised together with the benzotriazole monomers according to the invention, or alternatively they can be reacted with further monomers to ter- and quaterpolymers. The molecular weight of the polymers obtained, is of little importance provided that the minimum limiting values necessary to obtain the customary and essential mechanical and electrical properties are exceeded. Depending on the polymers, is should be between 5000 and several million.

The copolymerisation of the ethylenically unsaturated compounds with the 2-(2'-hydroxyphenyl)-benzotriazole compounds, which contain at least one copolymerisable ethylenically unsaturated group, is performed in the customary manner. It is initiated for example by means of free radicals, such as are formed for example with the heating of benzoyl peroxide, α,α'-azodiisobutyronitrile and tert-butyl peroxide, or in redox system, such as mixtures of salts of peroxysulfuric acid and sulfurous acid; or by the action of high energy radiation. In some cases, also ionic polymerisation is successful; however, this is difficult to perform on account of the strongly polar character of the monomeric 2-(2'-hydroxyphenyl)-benzotriazole compounds.

The processing of the polymers according to the invention is carried out in the customary manner, for example by injection moulding, moulding, calendering and casting. The polymers can also be further reacted to form homologous polymers: for example, polyvinyl esters can be saponified to form polyvinyl alcohols.

The initial physical properties of the novel addition polymers (with the exception of UV absorption) are very similar to those of the conventionally produced polymers, that is to say, produced in the absence of 2-(2'-hydroxyphenyl)-benzotriazole compounds incorporable by polymerisation. The processing can therefore in general be carried out in both cases in the same manner. On ageing under the influence of light, however, addition polymers according to the invention exhibit a considerably less variation of the original physical properties, and are moreover much less subject to the discolouration otherwise commonly occurring.

In general, copolymers according to the invention are used in the manner in which corresponding, conventionally produced polymers are used. There are however additional applications for the copolymers according to the invention by virtue of their stability to light and their UV absorption capacity, for instance as construction materials or coating materials, or as UV filters in the packing industry.

Together with the stabilisers according to the invention, there can also be added other additives, for example: antioxidants, other UV absorbers, metal carboxylates, lubricants, antistatic agents, flameproofing agents, pigments, fillers or reinforcing substances. Furthermore, crosslinking auxiliaries, for example triallylcyanurate, diallylterephthalate, triallyltrimethithate, ethylene glycol diacrylate or trimethylalpropane trimethacrylate.

There are listed below examples of further additives with which the benzotriazoles according to the invention can be used:

1. Antioxidants 1.1 Alkylated monophenols
2,6-di-tert-butyl-4-methylphenol,
2-tert-butyl-4,6-dimethylphenol,
2,6-di-tert-butyl-4-ethylphenol,
2,6-di-tert-butyl-4-n-butylphenol,
2,6-di-tert-butyl-4-i-butylphenol,
2,6-di-cyclopentyl-4-methylphenol,
2-(α-methylcyclohexyl)-4,6-dimethylphenol,
2,6-di-octadecyl-4-methylphenol,
2,4,6-tri-cyclohexylphenol,
2,6-di-tert-butyl-4-methoxymethylphenol.

1.2. Alkylated hydroquinones
2,6-di-tert-butyl-4-methoxyphenol,
2,5-di-tert-butyl-hydroquinone,
2,5-di-tert-amyl-hydroquinone,
2,6-diphenyl-4-octadecyloxyphenol.

1.3. Hydroxylated thiodiphenyl ethers
2,2'-thio-bis-(6-tert-butyl-4-methylphenol),
2,2'-thio-bis-(4-octylphenol),
4,4'-thio-bis-(6-tert-butyl-3-methylphenol),
4,4'-thio-bis-(6-tert-butyl-2-methylphenol).

1.4. Alkylidene-bisphenols
2,2'-methylene-bis-(6-tert-butyl-4-methylphenol),
2,2'-methylene-bis-(6-tert-butyl-4-ethylphenol), 2,2'-methylene-bis-[4-methyl-6-(α-methylcyclohexyl)-phenol],
2,2'-methylene-bis-(4-methylene-6-cyclohexylphenol),
2,2'-methylene-bis-(6-nonyl-4-methylphenol),
2,2'-methylene-bis-(4,6-di-tert-butylphenol),
2,2'-ethylidene-bis-(4,6-di-tert-butylphenol),
2,2'-ethylidene-bis-(6-tert-butyl-4-isobutylphenol),
2,2'-methylene-bis-[6-(α-methylbenzyl)-4-nonylphenol],
2,2'-methylene-bis-[6-(α,α-dimethylbenzyl)-4-nonylphenol],
4,4'-methylene-bis-(2,6-di-tert-butylphenol),
4,4'-methylene-bis-(6-tert-butyl-2-methylphenol),
1,1-bis-(5-tert-butyl-4-hydroxy-2-methylphenyl)-butane,
2,6-di-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane,
ethylene glycol-bis-[3,3-bis-(3'-tert-butyl-4'-hydroxyphenyl)-butyrate],
di-(3-tert-butyl-4-hydroxy-5-methylphenyl)-dicyclopentadiene,
di-[2-(3'-tert-butyl-2'-hydroxy-5'-methyl-benzyl)-6-tert-butyl-4-methyl-phenyl]terephthalate.

1.5 Benzyl compounds
1,3,5-tri-(3,5-di-tert-butyl-4-hydroxybenzyl)-2,4,6-trimethylbenzene,
di-(3,5-di-tert-butyl-4-hydroxybenzyl) sulfide,
isooctyl 3,5-di-tert-butyl-4-hydroxybenzyl-mercaptoacetate,
bis-(4-tert-butyl-3-hydroxy-2,6-dimethylbenzyl) dithiolterephthalate,
1,3,5-tris-(3,5-di-tert-butyl-4-hydroxybenzyl) isocyanurate,
1,3,5-tris-(4-tert-butyl-3-hydroxy-2,6-dimethylbenzyl) isocyanurate,
dioctadecyl 3,5-di-tert-butyl-4-hydroxybenzyl-phosphonate,
the calcium salt of monoethyl 3,5-di-tert-butyl-4-hydroxybenzyl-phosphonate.

1.6. Acylaminophenols
4-hydroxy-lauric acid anilide,
4-hydroxy-stearic acid anilide,
2,4-bis-octylmercapto-6-(3,5-di-tert-butyl-4-hydroxyanilino)-s-triazine,
octyl N-(3,5-di-tert-butyl-4-hydroxyphenyl)-carbamate.

1.7 Esters of β-(3,5-di-tert-butyl-4-hydroxyphenyl)-propionic acid with monohydric or polyhydric alcohols, for example with:

| methanol | diethylene glycol, |
| octadecanol | triethylene glycol, |
| hexane-1,6-diol, | pentaerythritol, |
| neopentyl glycol, | tris-hydroxyethyl-isocyanurate, |
| thiodiethylene glycol, | di-hydroxyethyl-oxalic acid diamide. |

1.8. Esters of β-(5-tert-butyl-4-hydroxy-3-methylphenyl)propionic acid with nonhydric or polyhydric alcohols, for example with:

| methanol | diethylene glycol, |
| octadecanol | triethylene glycol, |
| hexane-1,6-diol | pentaerythritol, |
| neopentyl glycol | tris-hydroxyethyl- |
| thiodiethylene glycol | isocyanurate, |
| | di-hydroxyethyl-oxalic acid diamide. |

1.9. Amides of β-(3,5-di-tert-butyl-4-hydroxyphenyl)-propionic acid, for example:
N,N'-di-(3,5-di-tert-butyl-4-hydroxyphenylpropionyl)-hexamethylenediamine,
N,N'-di-(3,5-di-tert-butyl-4-hydroxyphenylpropionyl)-trimethylenediamine,
N,N'-di-(3,5-di-tert-butyl-4-hydroxyphenylpropionyl)-hydrazine.

2. UV Absorbers and light stabilisers 2.1. 2-(2'-Hydroxyphenyl)-benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted or unsubstituted benzoic acids, for example: 4-tert-butyl-phenyl salicylate, phenyl salicylate, octylphenyl salicylate, dibenzoylresorcinol, bis-(4-tert-butylbenzoyl)-resorcinol, benzoylresorcinal, 3,5-di-tert-butyl-4-hydroxybenzoic acid-2,4-di-tert-butylphenyl ester and 3,5-di-tert-butyl-4-hydroxybenzoic acid hexadecyl ester.

2.4. Acrylates, for example ethyl or isooctyl α-cyano-β,β-diphenylacrylate, methyl α-carbomethoxy-cinnamate, methyl or butyl α-cyano-β-methyl-p-methoxycinnamate, methyl α-carbomethoxy-p-methoxy-cinnamate and N-(β-carbomethoxy-β-cyanovinyl)-2-methyl-indoline.

2.5. Nickel compounds, for example nickel complexes of 2,2'-thio-bis-[4-(1,1,3,3-tetramethylbutyl)-phenol], such as the 1:1 or 1:2 complex, with or without additional ligands, such as n-butylamine, triethanolamine or N-cyclohexyl-diethanolamine, nickel dibutyl-dithiocarbamate, nickel salts of monoalkyl, such as methyl or ethyl, 4-hydroxy-3,5-di-tert-butylbenzylphosphonates, nickel complexes of ketoximes, such as 2-hydroxy-4-methyl-phenylundecyl ketone oxime, and nickel complexes of 1-phenyl-4-lauroyl-5-hydroxyparazole, with or without additional ligands.

2.6 Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl)n-butyl-3,5-di-tert-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethylpiperidyl)-hexamethylenediamine and 4-tert-octylamino-2,6-dichloro-1,3,5-s-triazine, tris-(2,2,6,6-tetramethylpiperidyl)-nitrolotriacetate, tetrakis-(2,2,6,6-tetramethyl-4-piperidyl)-1,2,3,4-butanetetracarboxylic acid and 1,1'-(1,2-ethanediyl)-bis-(3,3,5,5-tetramethyl-piperazinone).

2.7. Oxalic acid diamides, for example 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)oxalamide, 2-ethoxy-5-tert-butyl-2'-ethyl-oxanilide and the mixture thereof with 2-ethoxy-2'-ethyl-5,4'-di-tert-butyl-oxanilide, and mixtures of ortho- and para-methoxy- and of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole and bis-benzylideneoxalic acid dihydrazide.

4. Phosphites and phosphonites, for example triphenyl phosphite, diphenyl alkyl phosphites, phenyl dialkyl phosphites, tri-(nonylphenyl) phosphite, trilauryl phosphite, trioctadecyl phosphite, distearyl pentaerythritol diphosphite, tris-(2,4-di-tert-butylphenyl) phosphite, diisodecyl pentaerythritol diphosphite, di-(2,4-di-tert-butylphenyl) pentaerythritol diphosphite, tristearyl sorbitol triphosphite and tetrakis-(2,4-di-tert-butylphenyl)-4,4'-biphenylene diphosphonite.

5. Compounds which destroy peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto) propionate.

6. Polyamide stabilisers, for example copper salts in combination with iodides and/or phosphorus compounds, and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal and alkaline-earth metal salts of higher fatty acids, for example C stearate, Zn stearate, Mg stearate, Na ricinoleate, K palmitate, antimony pyrocatecholate and tin pyrocatecholate.

8. Nucleating agents, for example 4-tert-butylbenzoic acid, adipic acid and diphenylacetic acid.

9. Fillers and reinforcing agents, for example calcium carbonate, silicates, glass fibers, asbestos, talc, kaolin, mica, barium sulfate, metal oxides and hydroxides, carbon black and graphite.

10. Other additives, for example plasticisers, lubricants, emulsifiers, pigments, optical brighteners, flameproofing agents, antistatic agents and blowing agents.

The following Examples further illustrate the present invention.

EXAMPLE 1

In 100 ml of methylene chloride at 0°–5° C. are dissolved 43.7 g (0.1 mol) of 3-(2H-benzotriazol-2-yl)-4-hydroxy-5-tert-butyl-benzenepropionic acid-(2-hydroxy)cyclohexyl ester and 13.3 g (0.105 mol) of chloropropionic acid chloride. There are slowly added dropwise at this temperature 21.1 g (0.21 mol) of triethylamine, and a precipitate of triethylamine hydrochloride is immediately formed. After the dropwise addition, the mixture is stirred cold for about 30 minutes, and the temperature is afterwards raised to 20°–25° C., stirring being maintained at this temperature for about a further 6 hours. The solution is subsequently filtered and is then washed with a diluted sodium carbonate solution. The organic phase is concentrated by evaporation, and the brownish resin is recrystallised from hexane to thus obtain 34.4 g (70.1% of theory) of 3-(2H-benzotriazol-2-yl)-4-hydroxy-5-tert-butyl-benzenepropionic acid-(2-acrylyloxy)-cyclohexyl ester as a white crystalline product, m.p. 82°–84° C.

EXAMPLE 2

When 3-(5-chloro-2H-benzotriazol-2-yl)-4-hydroxy-5-tert-butyl-benzenepropionic acid-(2-hydroxy)-cyclohexyl ester is used, the procedure otherwise being as described in Example 1, there is obtained 3-(5-chloro-2H-benzotriazol-2-yl)-4-hydroxy-5-tert-butyl-benzenepropionic acid-(2-acrylyloxy)-cyclohexyl ester as a white crystalline product, m.p. 109°–110° C.

EXAMPLE 3

When N-(hydroxyethyl)-3-(2H-benzotriazol-2-yl)-4-hydroxy-5-tert-butyl-benzenepropanamide is used, the procedure being otherwise as described in Example 1, there is obtained N-(2-acrylyloxyethyl)-3-(2H-benzotriazol-2-yl)-4-hydroxy-5-tert-butyl-benzenepropanamide as a white crystalline product, m.p. 80°–83° C.

EXAMPLE 4

When N-(2-hydroxyethyl)-3-(5-chloro-2H-benzotriazol-2-yl)-4-hydroxy-5-tert-butyl-benzenepropanamide is used, there is obtained, using the same process again, N-(2-acrylyloxyethyl)-3-(5-chloro-2H-benzotriazol-2-yl)-4-hydroxy-5-tert-butyl-benzenepropanamide as a white crystalline product, m.p. 106°–108° C.

EXAMPLE 5

When N-(3-hydroxypropyl)-3-(2H-benzotriazol-2-yl)-4-hydroxy-5-tert-butyl-benzenepropanamide is used, the procedure being otherwise as described in Example 1, there is obtained N-(3-acrylyloxypropyl)-3-(2H-benzotriazol-2-yl)-4-hydroxy-5-tert-butyl-benzenepropanamide as a white crystalline product, which is recrystallised from acetonitrile, m.p. 87°–89° C.

EXAMPLE 6

When 3-(2H-benzotriazol-2-yl)-4-hydroxy-5-tert-butyl-benzenepropionic acid-(2-hydroxy)-propyl ester is used, the procedure otherwise being exactly as described in Example 1, there is obtained 3-(2H-benzotriazol-2-yl)-4-hydroxy-5-tert-butyl-benzenepropionic acid-(2-acrylyloxy)-propyl ester as a resinous product.

Elementary analysis

| calculated: | found: |
|---|---|
| C = 66.50% | C = 66.51% |
| H = 6.47% | H = 6.62% |
| N = 9.31% | N = 9.27% |

EXAMPLE 7

When 3-(2H-benzotriazol-2-yl)-4-hydroxy-5-tert-butyl-benzenepropionic acid-(2-hydroxy)-butyl ester is used, the procedure otherwise being exactly as described in Example 1, there is obtained 3-(2H-benzotriazol-2-yl)-4-hydroxy-5-tert-butyl-benzenepropionic acid-(2-acrylyloxy)-butyl ester as a resinous product.

Elementary analysis:

| calculated: | found: |
|---|---|
| C = 67.98% | C = 67.28% |
| H = 6.71% | H = 6.68% |
| N = 9.03% | N = 9.07% |

EXAMPLE 8

When 3-(2H-benzotriazol-2-yl)-4-hydroxy-5-tert-butyl-benzenepropionic acid-(2-hydroxy-2-phenyl)-ethyl ester is used, the procedure being otherwise as described in Example 1, there is obtained 3-(2H-benzotriazol-2-yl)-4-hydroxy-5-tert-butyl-benzenepropionic acid-(2-acryloxy-2-phenyl)-ethyl ester as a white crystalline product, which is recrystallized from ligroin, m.p. 89°-91° C.

EXAMPLE 9

When 3-(2H-benzotriazol-2-yl)-4-hydroxy-5-tert-butyl-benzenepropionic acid-(2-hydroxy-3-phenoxy)-propyl ester is used, the procedure being otherwise exactly as described in Example 1, there is obtained 3-(2H-benzotriazol-2-yl)-4-hydroxy-5-tert-butyl-benzenepropionic acid-(2-acryloxy-3-phenoxy)-propyl ester.

EXAMPLE 10

38.2 g of N-(2-hydroxyethyl)-3-(2H-benzotriazol-2-yl)-4-hydroxy-5-tert-butyl-benzenepropanamide and 21.6 g of dimethyl maleate are dissolved in 300 ml of toluene. The solution is heated to refluxing temperature, and 1.24 g of dibutyltin oxide are added as catalyst. A mixture of methanol/toluene is subsequently distilled off for 5 hours, in the course of which pure toluene is continuously added through the dropping funnel, and eventually a beige-coloured precipitate is formed. After a reaction time of 5 hours, this precipitate is filtered off, and the orange-coloured filtrate is concentrated by evaporation. There is obtained a brownish oil, which is chromatographed through silica gel with $CH_2Cl_2$/ethyl acetate (9:1). The product fractions are combined, and concentrated by evaporation. The residue is recrystallised from hexane and a small amount of toluene. The yield is 26.3 g of N-(2-(4-methoxy-1,4-dioxo-cis-but-2-en-1-yloxy)ethyl)-3-(2H-benzotriazol-2-yl)-4-hydroxy-5-tert-butyl-benzenepropanamide as a white crystalline product, m.p. 72°-75° C.

EXAMPLE 11

Weathering-test results on acrylic resin films with a UV absorber incorporated by polymerisation Formulation: 82 parts of a polyester acrylate (Ebecryl 584 Fa. UCB)
15 parts dicyclopentenyloxyethylacrylate (Rohm + Haas),
3 parts of a levelling agent (Byk 300),
1.5 parts of the additive are homogenised for 5 minutes in a dissolver. The UV absorbers are added, and the mixture is again homogenised for 5 minutes in the dissolver at 45°-50° C.

Application

The clear lacquer is applied, with an electric-motor-driven, wire-wound coating rod, to a primed aluminium sheet coated with silver-metallic lacquer to thus obtain dry films of 40±3 μm. These are subsequently cured by electron beam radiation in a laboratory apparatus with 6M rad. The cured films are then irradiated in a QUV irradiation apparatus with the following cycle:

4 hours with UV light at 60° C.,
4 hours without irradiation at 50° C., and so forth.

The specimens are examined every 100 hours with respect to gloss retention and cracking.

| | Results | |
|---|---|---|
| | gloss retention % | visible cracking after |
| without additive | 40 | 300 h |
| additive Example 5 | >70 | >500 h |
| additive Example 6 | >70 | >500 h |
| additive Example 7 | >70 | >500 h |

What is claimed is:

1. A copolymer which comprises the copolymerization product of
   (a) an ethylenically unsaturated compound, and
   (b) a compound of formula I

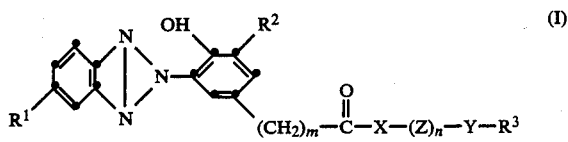

wherein
X is —O— or —N(R$^4$)—,
Y is —O— or —N(R$^5$)—,
Z is $C_2$–$C_6$-alkylene, 2-hydroxypropylene or cyclohexylene,
m is 2,
n is 1,
R$^1$ is hydrogen or chlorine,
R$^2$ is tert-butyl,
R$^3$ is a —C(O)—C(R$^6$)=C(H)R$^7$ group, wherein R$^6$ and R$^7$ independently of one another are hydrogen or methyl, or
R$^3$, when Y is —N(R$^5$)—, forms together with R$^5$ a group —C(O)—CH=CH—C(O)—, and
R$^4$ and R$^5$ independently of one another are hydrogen or $C_1$–$C_4$-alkyl.

* * * * *